(12) United States Patent
Cappella et al.

(10) Patent No.: US 9,610,394 B2
(45) Date of Patent: Apr. 4, 2017

(54) APPARATUS FOR EXTRACORPOREAL BLOOD TREATMENT

(71) Applicant: GAMBRO LUNDIA AB, Lund (SE)

(72) Inventors: Rocco Cappella, Termoli (IT); Mirco Lancellotti, Bomporto (IT)

(73) Assignee: Gambro Lundia AB, Lund (SE)

( * ) Notice: Subject to any disclaimer, the term of this patent is extended or adjusted under 35 U.S.C. 154(b) by 231 days.

(21) Appl. No.: 14/368,867

(22) PCT Filed: Dec. 27, 2012

(86) PCT No.: PCT/IB2012/057759
§ 371 (c)(1),
(2) Date: Jun. 26, 2014

(87) PCT Pub. No.: WO2013/098779
PCT Pub. Date: Jul. 4, 2013

(65) Prior Publication Data
US 2014/0358061 A1 Dec. 4, 2014

(30) Foreign Application Priority Data
Dec. 30, 2011 (IT) .............................. MI2011A2455

(51) Int. Cl.
*A61M 1/36* (2006.01)
*A61M 1/30* (2006.01)
*A61M 1/14* (2006.01)

(52) U.S. Cl.
CPC ............ *A61M 1/3653* (2013.01); *A61M 1/30* (2013.01); *A61M 1/302* (2014.02); *A61M 1/303* (2014.02);
(Continued)

(58) Field of Classification Search
CPC ........ A61M 1/14; A61M 1/16; A61M 1/1601; A61M 1/1603; A61M 1/1611; A61M 1/30;
(Continued)

(56) References Cited

U.S. PATENT DOCUMENTS 4,486,189 A * 12/1984 Troutner ................. A61M 1/30
128/DIG. 3
4,599,165 A 7/1986 Chevallet
(Continued)

FOREIGN PATENT DOCUMENTS

DE 100 42 324 C1 2/2002
DE 10 2007 026010 12/2008
(Continued)

*Primary Examiner* — Tatyana Zalukaeva
*Assistant Examiner* — Benjamin Klein
(74) *Attorney, Agent, or Firm* — Mueting, Raasch & Gebhardt, P.A.

(57) ABSTRACT

An apparatus is described for extracorporeal blood treatment comprising an extracorporeal circuit (2), a first pump (13) operating at the removal line (3) of the blood, a second pump (14) operating at the return line (7) of the blood to the patient, a first blood reservoir (21) operating on the blood return line (7) upstream of the second blood pump (14) and a sensor (22) predisposed to detect at least a parameter, for example the pressure in the first reservoir; a control unit (100) connected to the first pump (13), to the second pump (14) and to the sensor (22) is configured such as to control the first pump (13) to promote removal of the blood along the removal line and the movement of the second pump (14) to promote the return of the blood to the patient along the return line, the control of the second pump being carried out on the basis of the signal emitted by the sensor acting on the first reservoir.

21 Claims, 4 Drawing Sheets

(52) U.S. Cl.
CPC ............ *A61M 1/306* (2014.02); *A61M 1/308* (2014.02); *A61M 1/3624* (2013.01); *A61M 1/3639* (2013.01); *A61M 1/14* (2013.01); *A61M 1/3621* (2013.01); *A61M 2205/50* (2013.01)

(58) Field of Classification Search
CPC ...... A61M 1/303; A61M 1/306; A61M 1/308; A61M 1/34; A61M 1/341; A61M 1/36; A61M 1/3621; A61M 1/3624; A61M 1/3639; A61M 1/3653
See application file for complete search history.

(56) References Cited

U.S. PATENT DOCUMENTS 6,645,166 B2    11/2003   Scheunert
8,632,487 B2     1/2014   Gunther

FOREIGN PATENT DOCUMENTS

EP           0 240 101 A2    10/1987
WO    WO 2011/076511      6/2011

\* cited by examiner

APPARATUS FOR EXTRACORPOREAL BLOOD TREATMENT

This application is a U.S. National Stage Application of International Application No. PCT/IB2012/057759, filed Dec. 27, 2012, which was published in English on Jul. 4, 2013 as International Patent Publication WO 2013/098779 A1. International Application No. PCT/IB2012/057759 also claims priority to Italian Application No. MI2011A002455 filed Dec. 30, 2011.

FIELD OF THE INVENTION

The invention relates to an apparatus for extracorporeal blood treatment, for example by dialysis, hemofiltration, hemodiafiltration, ultrafiltration, plasmapheresis, oxygenation or more besides, in which blood removed from a patient or a donor is extracted from the patient and transported towards a treatment unit: for this purpose, the apparatus of the invention comprises an extracorporeal blood circuit which may be configured in both single-access mode (for example with a needle or another single access organ) and in a double access mode (for example with a needle or another vascular access organ located on the blood removal line from the patient and a needle or another vascular access organ located on the patient blood return line).

BACKGROUND OF THE INVENTION

As is known, apparatus for extracorporeal blood treatment typically comprise at least a blood removal line from the patient, at least a treatment unit where the blood removed from the patient is sent, and at least a return line for the treated blood to the patient. According to the types of treatment to be performed, the treatment unit may comprise an ultrafilter, a plasma filter, a hemofilter, a hemodiafilter, or another treatment unit. With the aim of connecting the blood removal line and the blood return line with the cardiovascular system of the patient, vascular access organs are used, such as for example needles, catheters, cannulas or other organs besides, which suitably inserted in a blood vessel that is a part of the cardiovascular system of the patient, enable removal of the blood to be treated and the return of the treated blood to the patient.

For example a first access organ may be terminally connected to the blood removal channel from the patient, and a second access organ may be connected to the blood return line to the patient: these access organs are inserted into the patient's cardiovascular system, for example at a fistula, and thus they enable removal of the blood and return of the blood to the patient.

It is clear that in the described system a double access must be made on the patient, one for the first access organ and one for the second access organ. As some patients have difficulty in contemporaneously receiving two access organs, processes and apparatus have been developed which use extracorporeal circuits having a single access to the patient: in this case, the single access is used both for removing the blood to be treated and for returning the treated blood to the patient. As the same vascular access is used for the double function of removing and returning the blood, the access organ is suitably connected with the extracorporeal circuit: further, the control of the removal and the return of the blood are coordinated according to temporally alternated stages.

A known technical solution described in U.S. Pat. No. 4,599,165 comprises using the extracorporeal circuit in a single access configuration; in this solution a dialysis apparatus is provided, in which the extracorporeal circuit exhibits a single needle and a first blood pump is predisposed to operate on the blood removal line from the patient, while a second blood pump is predisposed to return the blood to the patient and operates on the return line located downstream of the blood treatment unit which, in the example, comprises a hemodialyzer. The two pumps are active alternatively such that in a first stage there is blood removal into the extracorporeal circuit and in a second stage there is return of the blood to the patient.

In the apparatus operating with a single vascular access, when the user passes from the single-access mode to the double-access mode (in which an access is dedicated to the blood removal line and another to the blood return line) a problem arises linked to the pump present on the blood return line to the patient, as in the double-access mode the removal and return of the blood have to be done contemporaneously. In this regard, it is worthy of note that the pumps used in extracorporeal blood circuits are mostly occlusive pumps, for example peristaltic pumps, that when not moved prevent passage of fluid through the tract of tube on which the pumps operate. Should it be desired to pass from a single-access operating mode to a double-access operating mode, the situation would arise in which when the first pump located on the blood removal line is in operation, the second pump constitutes, in effect, an obstacle to the return of the treated blood to the patient.

Likewise, if the second pump were to be in operation, the first pump would constitute an obstacle to the aspiration of the blood from the patient. With the aim of obviating this type of drawback, the extracorporeal blood treatment systems in use at present comprise using exclusively the blood pump located on the blood removal line from the patient and controlling the motion thereof according to a predetermined revolution rate set by the operator or deduced by the machine on the basis of the blood flow rate desired by the operator. Vice versa, the pump located on the blood return branch to the patient is manually disengaged from the respective tube segment, such that the intervention of the pump is excluded and thus the tube segment is completely free of the occlusive action of the pump. Although the above-described solution has been adopted in the past, it exhibits some drawbacks.

Firstly, the passage from a single vascular-access mode towards a double vascular-access mode involves manual intervention by an operator who has to disengage the pump from the respective tract of tube. Consequently, should the operator not intervene by timely disengaging the tract of tube associated to the second pump, there would inevitably ensue a situation in which the pump would occlude the respective tract of tube during the treatment, thus causing interruption of the treatment itself with a consequent machine halt. Further, even should an operator intervene adequately, it is clear that the above-described procedure leads to an intervention on the part of the operator, with a consequent impossibility of automating the process and slowness in the performing of the passage from single-vascular-access to double-vascular-access.

OBJECT OF THE INVENTION

An object of the invention is to disclose an apparatus for extracorporeal blood treatment and a process for control thereof which are able to solve one or more of the cited drawbacks.

A further aim of the invention is to make available an apparatus for extracorporeal blood treatment and a process for control thereof which enable performing passage from the single-access configuration towards the double-access configuration in a safe and efficient manner.

An additional aim is to define an apparatus for extracorporeal blood treatment and a process for control thereof which enable repeatedly and efficiently performing the passage from the single-access configuration towards the double-access configuration and vice versa.

A further aim of the invention is to disclose an apparatus and a control process of the apparatus which are able to significantly increase the degree of automation in the passage from the single-vascular-access configuration to the double-vascular-access.

An auxiliary aim of the invention is to disclose an apparatus and a control procedure therefor which are easy to implement.

At least one of the above-specified aims is substantially attained by an apparatus for extracorporeal blood treatment and by a process for control thereof, according to one or more of the claims.

Other aspects of the invention are illustrated in the following.

A first aspect of an apparatus for extracorporeal blood treatment comprises:
- a blood removal line having an end configured to be connected to a cardiovascular system of a patient;
- at least a blood treatment unit comprising a semipermeable membrane which divides the unit itself into a first and a second chamber, the first chamber being connected to a second end of the blood removal line of the patient;
- a return line of the treated blood to the patient having a first end connected to the first chamber of the blood treatment unit and a second end destined to be connected to the cardiovascular system of the patient;
- at least a first pump operating on the blood removal line;
- at least a second pump operating on the blood return line to the patient;
- a discharge line connected to the second chamber of the treatment unit for receiving waste blood in outlet from the unit;
- at least a first blood reservoir operating on the blood return line upstream of the second blood reservoir;
- at least a sensor predisposed to detect at least a parameter selected from among a group comprising:
  - a pressure present in the first reservoir,
  - a blood level present in the first reservoir,
  - a blood volume present in the first reservoir,
  - a pressure in a tract of the return line upstream of the second pump,
  and predisposed to emit a signal corresponding to a measured value of the parameter;
- a control unit connected to the first pump, to the second pump and to the sensor, wherein the control unit is configured such as to operate in a first operating mode, corresponding to a single-access configuration of the extracorporeal circuit, and in a second operating mode, corresponding to a double-access configuration of the extracorporeal circuit, the control unit, in the second operating mode, being configured to carry out following steps:
  - receiving the signal emitted by the sensor,
  - controlling the first pump such as to promote the removal of blood from the patient along the blood removal line;
  - controlling the second pump such as to promote return of the blood to the patient along the return line, the control of the second pump being carried out on the basis of the signal emitted by the sensor acting on the first reservoir.

In a 2nd aspect, according to the 1st aspect, the treatment unit comprises a semi-permeable membrane which divides the unit into a first and a second chamber, the first chamber being connected to a second end of the blood removal line and with a first end of the blood return line.

In a 3rd aspect according to any one of the preceding aspects the apparatus comprises a second reservoir operating on the blood removal line from the patient and arranged upstream with respect to the first chamber and downstream of the first pump.

In a 4th aspect according to any one of the preceding aspects, the apparatus further comprises: a first flow check organ operating on the removal line upstream of the first pump and at least a second flow check organ operating on the blood return line downstream of the second pump, the control unit being connected to the first and second flow check organ in order to selectively command opening and closure thereof and consequently to determine passage or prevention of the passage of fluid in the respective lines on which the check organs operate.

In a 5th aspect, according to the preceding aspect, the control unit in the first operating mode is configured to performing following steps:
a) commanding closure of the second check organ, commanding opening of the first check organ, moving the first pump such as to command a fluid removal from the cardiovascular system of the patient through the removal line and the consequent increasing of the fluid level in the first and, if present, the second reservoir, and verifying the reaching of a predetermined maximum value of the parameter;
b) on reaching the predetermined maximum value of the parameter, commanding closure of the first flow check organ, halting the first pump, opening of the second flow check organ and movement of the second pump for transferring fluid through the return line towards the cardiovascular system of the patient, and verifying the reaching of a predetermined minimum value of the parameter.

In a 6th aspect according to the preceding aspect, on reaching the predetermined minimum value of the parameter, the control unit is configured to repeat stages a) and b).

In a 7th aspect according to any one of the preceding aspects, the apparatus comprises at least a user interface connected to the control unit such as to communicate thereto input commands entered by an operator, and/or such as to visualise or signal output information.

In an 8th aspect according to the preceding aspect, the control unit, at least during the second operating mode, is configured to control the first pump according to one selected from among a group comprising:
a. an inlet value set by an operator via the user interface,
b. a measured pressure value in a tract of the blood removal line located upstream of the first pump,
c. both said pressure value and the set value for blood flow entered by an operator via the user interface.

In a 9th aspect according to any one of the preceding aspects, the control unit is configured to receive an identifying command of passage from a configuration with a single vascular access to a configuration with a double vascular access and wherein, responsive to said command, the control unit is configured to operate in the second mode.

In a 10th aspect according to any one of the preceding aspects in which, in the second mode, the control unit is configured to control the second pump in order to maintain the value of the parameter substantially constant or within a predetermined range.

In an 11th according to any one of the preceding aspects, the parameter is the pressure detected in the first reservoir.

In a 12th aspect according to any one of the preceding aspects, the apparatus comprises at least a third pump acting on the waste line, the control unit being configured such as to receive from the user interface one from:
  a desired weight loss rate,
  a pair of values relating to an overall weight loss and to a treatment time in which the overall weight loss is to be achieved,
the control unit also being configured such as to control the third pump either according to the weight loss amount set or according to the pair of values relating to the overall weight loss and the treatment time. In practice, on the one hand the control unit controls the third pump such as to generate a desired ultrafiltration rate and on the other hand it controls the second blood pump such as to maintain the measured value of the parameter substantially constant or within a predetermined range.

In a 13th aspect according to any one of the preceding aspects, the apparatus comprises at least a first auxiliary reservoir operating in the blood return line downstream of the tract thereof on which the second pump operates and at least a second auxiliary reservoir operating in the blood removal line in a tract thereof upstream of the tract where the first pump operates.

In a 14th aspect according to any one of the preceding aspects the apparatus comprises at least an auxiliary pressure sensor operating at the first auxiliary reservoir and at least a second auxiliary pressure sensor, operating at the second auxiliary reservoir, the first and second auxiliary sensors being connected to the control unit.

In a 15th aspect according to any one of the preceding aspects, the control unit, in the second operating mode, is configured such as to carry out the following steps:
  commanding the first and the second flow check organs in open conditions;
  commanding the rotary movement of the first pump according to a set value of blood flow rate and/or a measured value of pressure in a tract of the removal line upstream of the tract in which the first pump operates;
  commanding the second blood pump in a rotary movement in the same direction as the rotary movement of the first blood pump, controlling the second pump such as to maintain the value of the parameter substantially constant or within a predetermined range.

In a 16th aspect according to any one of the preceding aspect, in the second mode, the control unit is configured for:
  comparing a measured value of the parameter with a desired reference value in order to determine any possible errors,
  generating a control value of the rotation velocity to be set on the second pump, the control value being generated as a function of the error,
  controlling the second pump, using the control value, In a 17th aspect the control unit is configured such as to repeat, for example periodically or at regular intervals, the steps of the preceding aspect.

In an 18th aspect, according to any one of the preceding aspects the control value is determined by the control unit as an integral function and/or as a proportional function of the error.

In a 19th aspect according to any one of the preceding aspects, the control value is compared by the control unit with a range of acceptability before being applied for control of the angular velocity of the second blood pump.

In a 20th aspect according to any one of the preceding aspects, it is provided a blood treatment process using an apparatus according to any one of the preceding aspects.

In a 21st aspect according to the preceding aspect, the process comprises following stages:
  configuring the extracorporeal circuit comprising the removal line and the return line in a single-needle configuration,
  performing the removal and return of blood with respect to the cardiovascular system of the patient according to blood removal and return stages that are sequentially alternated,
  configuring the extracorporeal circuit in a double-access configuration,
  carrying out the blood removal and return by contemporaneously moving the first and the second pump in a same rotation direction such as to determine a continuous removal and return of the blood to the patient, controlling the second pump such as to maintain the value of the parameter detected by the sensor substantially constant or within a predetermined range.

In a 22nd aspect according to aspect 20 or 21, the process comprises cyclically carrying out the following steps when the extracorporeal circuit is configured with a single access:
  commanding closing of the second check organ;
  commanding opening of the first check organ;
  moving the first pump such as to command a fluid removal from the cardiovascular system of the patient through the removal line and the consequent raising of the fluid level in the first and, if present, in the second reservoir,
  verifying reaching of a predetermined maximum value of the parameter;
  on reaching the predetermined maximum value of the parameter, commanding the closing of the first flow check organ, the halting of the first pump, the opening of the second flow check organ and the movement of the second pump with the aim of transferring fluid through the return line towards the cardiovascular system of the patient, and verifying the reaching of a predetermined minimum value of the parameter.

In a 23rd aspect according to the preceding aspect, the process comprises cyclically performing the following steps when having to pass from the single-access configuration to the double-access configuration:
  opening both the flow check organs and controlling the first pump such as to promote movement of liquid from the first end of the removal line towards the treatment unit,
  controlling the movement of the second pump in order to promote the blood return to the patient along the return line from the treatment unit towards the second end of the return line; the control of the second pump is performed in such a way as to maintain the parameter detected by the sensor substantially constant or within a predetermined range. In a case where the parameter is the pressure, the angular velocity of the second pump is regulated by periodically verifying that the real pressure measured by the sensor is substantially constant or lies within an acceptable pressure range.

DESCRIPTION OF THE DRAWINGS

A description of some embodiments and some aspects of the invention will be carried out in the following, with reference to the accompanying drawings, supplied purely by way of non-limiting example, in which.

DETAILED DESCRIPTION

Figure 1:
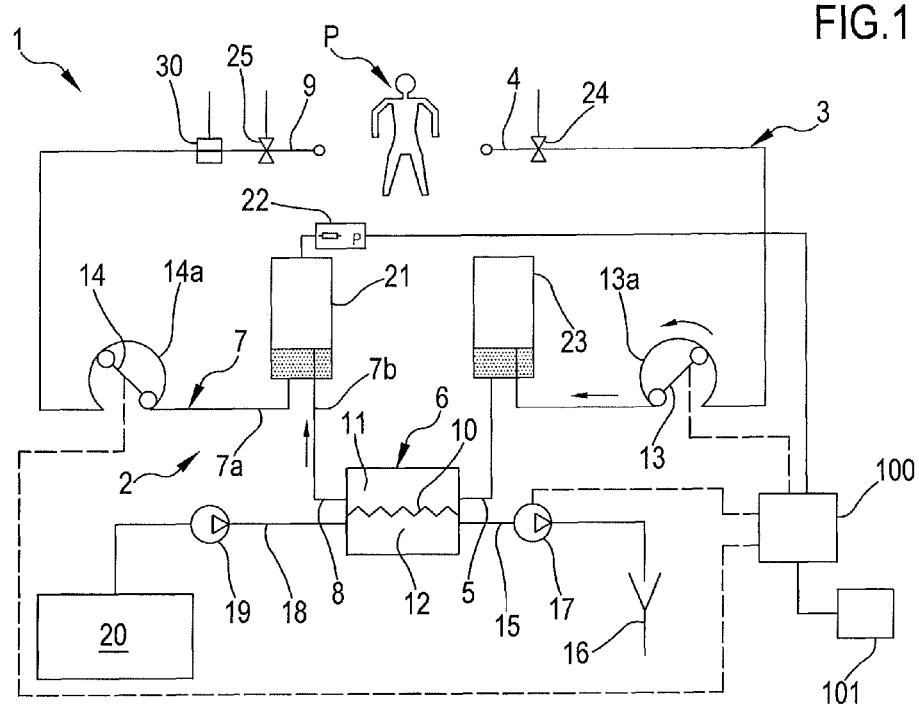
FIG. 1 is a representative diagram of an apparatus for extracorporeal blood treatment in a first embodiment.
Figure 2:
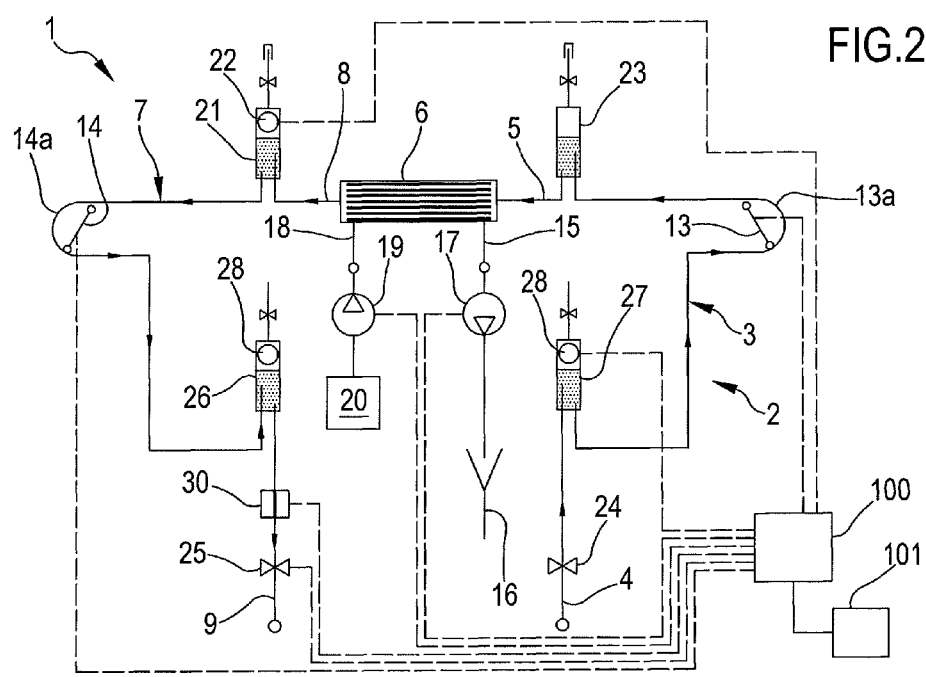
FIG. 2 is an illustrative diagram of an apparatus for extracorporeal blood treatment according to a second embodiment.

With reference to the figures of the drawings, 1 denotes in its entirety an apparatus for extracorporeal blood treatment. The apparatus 1 comprises an extracorporeal circuit 2 destined to extract blood to be processed from the cardiovascular system of a subject, for example a patient P, and return the blood after treatment to the patient. The extracorporeal circuit 2 comprises a blood removal line 3 having an end 4 destined to be connected with a cardiovascular system of the patient P and an end 5 connected with a treatment unit 6. The extracorporeal circuit 2 further comprises also a return line 7 of the blood to the patient having a first end 8 connected to the blood treatment unit 6 and a second end 9 destined to be connected to the cardiovascular system of the patient P. The treatment unit may for example comprise a filter for dialysis or a hemofilter or a plasma filter, or a membrane oxygenator or a hemodiafilter, or other units destined to process the blood removed from the patient.

In the illustrated examples, reference is made, by way of non-limiting example, to treatment units 6 having a semipermeable membrane 10 which divides the unit itself into a first and a second chamber 11 and 12: the first chamber is connected to the second end 5 of the blood removal line from the patient and to the first end 8 of the blood return line to the patient. As may be seen in FIGS. 1-5, the apparatus 1 comprises at least a first actuator, in the example a first pump 13, operating at the blood removal line to promote the movement of blood removed from the patient from the first end 4 of the removal line towards the first chamber: for example the first pump 13 is peristaltic pump that is active, as shown in FIGS. 1-5, on a respective tract of tube 13a and is able, when moved in an anti-clockwise direction, to move a blood flow along the removal line towards the first chamber 11.

The apparatus 1 further comprises at least a second actuator, in the example a second pump 14, operating at the blood return line to the patient; the second pump 14 is also for example a peristaltic pump active, as shown in FIGS. 1-5, on a respective tract of tube 14a and able, when moved in an anti-clockwise direction, of moving a blood flow along the return line from the first chamber 11 towards the second end 9 of the return line.

Note that for the purposes of the present description and the claims, the terms "upstream" and "downstream" are used with reference to relative positions assumed by components which are part of or which operate on the extracorporeal circuit 2. These terms are understood to refer to a direction of the flow from the first end 4 of the removal line towards the first chamber 11 and then towards the second end 9 of the return line.

Still with reference to the accompanying figures of the drawings, the apparatus 1 may comprise a discharge line 15 connected in outlet from the second chamber 12 of the treatment unit 6: the discharge line receives the waste fluid coming from the second chamber of the unit 6 and, for example, comprising used dialyser liquid and/or liquid that has been ultra-filtered through the membrane 10. The discharge line 15 leads to a receiving element 16, for example constituted by a collection bag or a discharge tubing of the waste fluid. One or more pumps 17 may operate on the discharge line: for example in accompanying FIGS. 1-5 a third pump 17 is provided, acting on the line 15.

Note that the structure of the discharge line may also be different from what is described above (as long as it is capable of adequately removing the fluid in outlet from the second chamber 12): for example the discharge line may comprise a single line as shown in the figures or a main discharge line and an ultrafiltration line which branches off the main discharge line and which is provided with a respective pump (solution not illustrated).

The apparatus 1 may also comprise a dialysis line 18 provided with a dialysis pump 19 and destined to receive a fresh fluid from a module 20, for example a bag or an in-line dialysis liquid preparation section, and send the fluid in inlet to the second chamber 12.

Finally, the apparatus 1 may comprise one or more infusion lines of a replacement fluid: for example it may comprise an infusion line connected to the removal line and/or an infusion line connected to the blood return line: these lines are not represented in the figures, nor are they further treated as they are not relevant to the purposes of the description of the present invention.

Returning to the structure of the extracorporeal circuit 2, the circuit 2 comprises at least a first blood reservoir 21 operating on the blood return line 7, upstream of the second blood pump 14, i.e. between the second blood pump 14 and the first end 8 of the return line 7; at least a sensor 22 is predisposed to detect at least a parameter relating to the fluid present in the first reservoir. The parameter may be the pressure in the first reservoir 21, the blood level present in the first reservoir 21, the blood volume present in the first reservoir 21: in the illustrated examples the sensor uses a pressure transducer and the first parameter is therefore constituted by the pressure measured at the first reservoir. In general, however, the sensor 22 is configured such as to emit a signal corresponding to a measured value of the parameter, and sending it to a control unit 100. Note that should the detected parameter be the pressure, the detection of the parameter may be made even very closely to the first reservoir 21, for example by means of a transducer located either in the tract of tube 7a between the second pump 14 and the first reservoir 21 or in the tract of tube 7b between the first reservoir 21 and the first end 8.

In the example of FIGS. 1-5, the extracorporeal circuit 2 comprises a second reservoir 23 operating on the blood removal line of patient, and arranged upstream with respect to the first chamber 11, between the second end 5 of the removal line and the first pump 13. Further, with the aim of operating in both single-vascular-access mode and in double-vascular-access mode, the apparatus further comprises a first flow check organ 24 operating on the removal line 3 upstream of the first pump and at least a second flow check organ 25 operating on the return line 7 of the blood to the patient downstream of the second pump 14. The check organs, constituted for example by a respective clamp commanded by the control unit 100, are arranged in proximity of the ends 4 and 9 of the respective lines and, during the single-access operating mode, are commanded sequentially to open and close as will be more fully described in the following.

FIGS. 2-5 show a variant of the apparatus of FIG. 1 in which the use of at least a first auxiliary reservoir 26 is comprised, operating in the blood return line 7 downstream of the tract 14a on which the second pump operates 14 and at least a second auxiliary reservoir 27 operating in the blood return line 3 upstream of the tract 13a where the first pump 13 operates. In practice, the first pump 13 and the relative tract of tube 13a are interposed between the second reservoir 23 and the second auxiliary reservoir 27, while the second pump 14 and the relative tract of tube 14a are interposed between the first reservoir 21 and the first auxiliary reservoir 26 such that the second auxiliary reservoir receives blood coming from the first end 4 and sends blood in outlet towards the inlet of the second reservoir which is connected in outlet to the inlet of the first chamber 11, in turn connected in outlet with the inlet of the first reservoir 21, which has an outlet connected to the inlet of the first auxiliary outlet, the outlet of which is connected to the second end 9 of the return line 7. With the aim of controlling the pressure regime at the various points of the extracorporeal circuit, an auxiliary pressure sensor 28 may be provided, operating at the first auxiliary reservoir 26, and a second auxiliary pressure sensor 29 may operate at the second auxiliary reservoir 27.

Control Unit

The control unit 100 may comprise one or more digital units, for example of the microprocessor type, or one or more analogical units, or a suitable combination of digital and analog units. As illustrated in the examples of FIGS. 1-5, the control unit 100 is connected with the first, the second and the third pump 13, 14 and 17 as well as with the sensor 22 and possibly, if present, with the auxiliary pressure sensors; the control unit 100 is configured or programmed such as to perform the procedures described herein below. In a case in which the control unit is programmable, the unit is connected with a data support for storing instructions that, when carried out by the control unit, determine carrying-out of the procedures which will be described in the following. The data support may comprise a mass memory, for example optical or magnetic, a re-programmable memory (EPROM, FLASH) or a memory of another nature besides.

The control unit 100 is configured such as to operate in a first operating mode, corresponding to a single-access configuration of the extracorporeal circuit, i.e. a configuration in which the ends 4 and 9 respectively of the removal line and the return line are connected to a single vascular access which may for example be a catheter, a cannula, a needle or another device able to connect the cardiovascular system of the patient with the ends 4 and 9.

The control unit 100 is also configured such as to operate in a second operating mode, corresponding to a double-access configuration of the extracorporeal circuit, i.e. to a configuration in which the ends 4 and 9 respective of the removal line and the return line are connected to a respective vascular access which may for example be a catheter, a cannula, a needle or another device able to connect two points of the cardiovascular system of the patient with the ends 4 and 9. In practice, with reference to FIGS. 1 and 2, in the case of single access the two ends 4 and 9 are connected to a same internal path of a needle, catheter or other vascular access, while in the case of double access the ends 4 and 9 are connected to respective distinct passages obtained in two separate access organs (for example two needles) or in a same organ (for example a double-channel intravascular catheter).

When the control unit operates with an extracorporeal circuit having a double-access configuration (see for example FIG. 5) it is configured to operate in the second mode as described herein below. The control of the first pump is done in such a way as to promote the movement of liquid from the first end 4 towards the first chamber 11. The control is, for example, performed in an open loop, on the basis of a desired flow inlet value which is pre-memorised or set by an operator, for example via a user interface 101 connected to the control unit: alternatively the control on the first pump may be based on a measured pressure value prevailing in a tract of the blood removal line located upstream of the first pump, or both on the basis of a desired inlet value and a measured value of pressure prevailing in the tract of the removal line upstream of the first pump 13.

Note that the pressure value in the tract of removal line upstream of the pump may be detected by the pressure sensor 29. In practice, the control unit receives the desired flow value and calculates the number of revolutions to be set on the first pump on the basis of the desired flow, also eventually taking account of the pressure upstream of the first pump. The control unit further receives the signal emitted by the sensor 22 and controls the movement of the second pump 14 such as to promote return of the blood to the patient along the return line from the first chamber 11 towards the second end 9 of the return line 7.

The second pump is controlled on the basis of the signal emitted by the sensor acting on the first reservoir. For example, the control unit may be configured such as to control the second pump 14 in such a way as to maintain substantially constant or with a predetermined range the value of the parameter detected by the sensor 22. In the case that the parameter is actually the pressure, the control unit regulates the angular velocity of the second pump with a closed-loop control, periodically verifying that the real pressure measured by the sensor 22 is substantially constant or lies within an acceptable pressure range.

Whether the controlled parameter is the pressure or another parameter, the control by the control unit is performed in a closed loop: in particular the control unit 100 is configured such as cyclically to perform, for example at predetermined time intervals, the following steps:
  a. Comparing a measured value of the parameter with a desired reference value in order to determine any possible errors, ("err" in FIG. 6),
  b. generating a control value of the rotation velocity ("u_Eff" in FIG. 6) to be set on the second pump 14, the control value being generated according to the error,
  c. comparing control value u_Eff to a range of acceptability (u_Min; u_Max) before being applied to the second blood pump,
  d. controlling the angular velocity of the second pump using the control value u_Eff.

Figure 6:
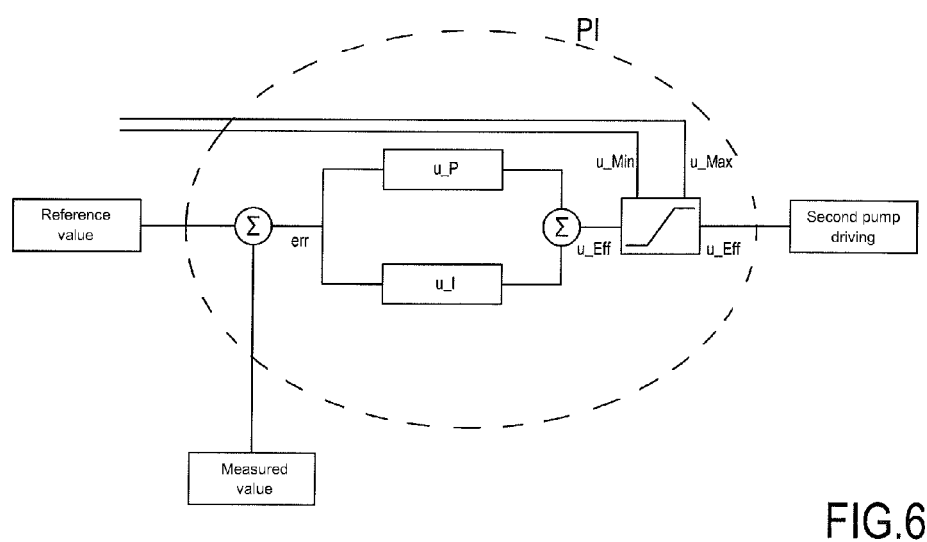
FIG. 6 is a control diagram of the second pump located on the blood return line in the apparatus illustrated schematically in FIG. 1 or in FIG. 2.

The diagram of FIG. 6 shows what is described: furthermore, note how the control value may be determined as an integral function and/or as a proportional function of the error.

As has been mentioned, the control unit 100 is also connected to the first and the second flow check organs 24 and 25 for selectively commanding the opening and closing and for consequently determining the passage or blocking of the fluid passage in the respective line on which the check organs operate. In the second operating mode of the control unit, the organs are maintained open such as to allow the blood to flow continuously through the extracorporeal circuit, while in the first operating mode the check organs are alternatively opened and closed such as to enable steps of loading and unloading the reservoirs, as described above. The check organs 24 and 25 are also used for safety purposes: for example the apparatus may comprise an air-bubble sensor 30 connected to the control unit 100 and capable of generating a signal which if greater than a certain threshold determines generation of a closing command of the organ 25 and eventually even a halting of the pumps 13 and 14. The check organs intervene when the apparatus operates with an extracorporeal circuit configured with a single access (see for example FIG. 3 and FIG. 4): in this case the control unit is in the first operating mode and is configured such as cyclically to perform to following steps:

a) commanding the closing of the second check organ, commanding the opening of the first check organ, moving the first pump such as to command a fluid removal from the cardiovascular system of the patent via the removal line and the consequent raising of the fluid level in the first and, if present, in the second reservoir, and verifying the reaching of a predetermined maximum value of the parameter;

b) on reaching the predetermined maximum value of the parameter, commanding closure of the first flow check organ, the halting of the first pump, the opening of the second flow check organ and the movement of the second pump with the aim of transferring fluid through the return line towards the cardiovascular system of the patient, and verifying the reaching of a predetermined minimum value of the parameter.

Figure 3:
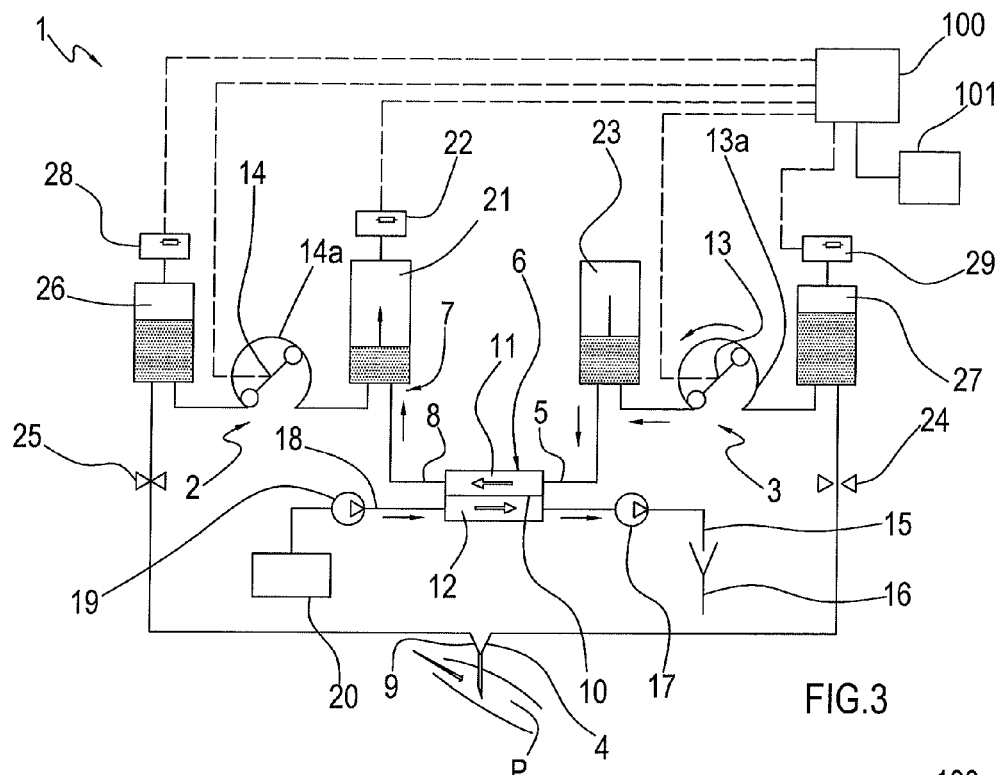
FIG. 3 schematically represents the apparatus for extracorporeal blood treatment of FIG. 2 in a single-needle configuration and in a first operating stage.
Figure 4:
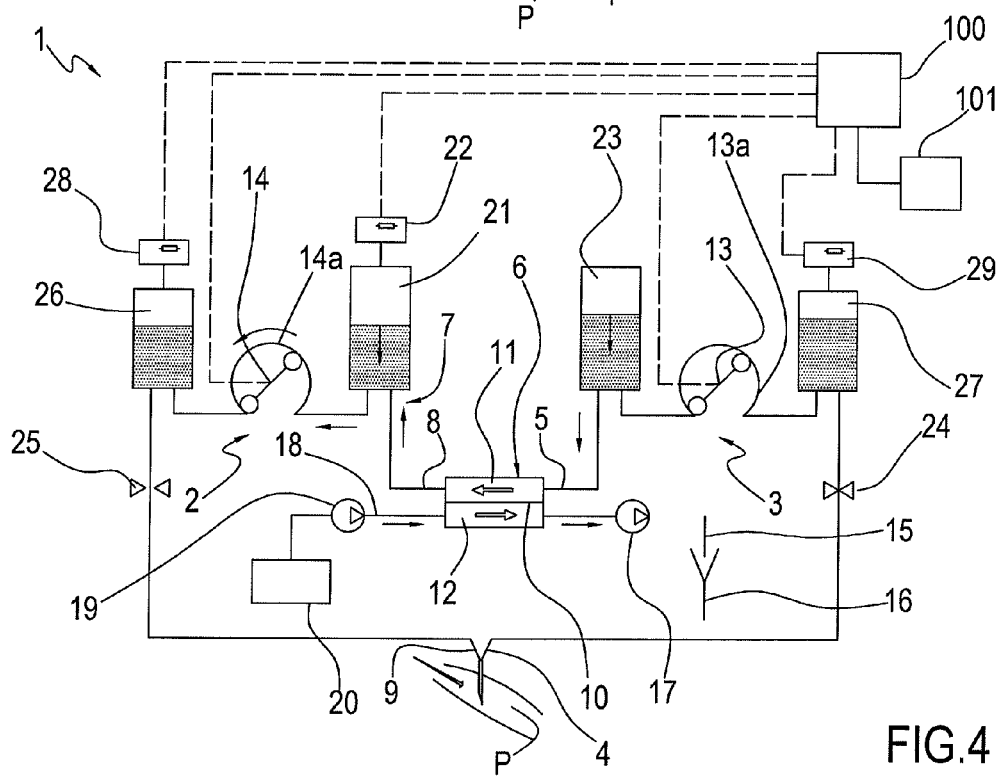
FIG. 4 schematically represents the apparatus for extracorporeal blood treatment of FIG. 2 in a second operating stage, again in the single-needle configuration.
Figure 5:
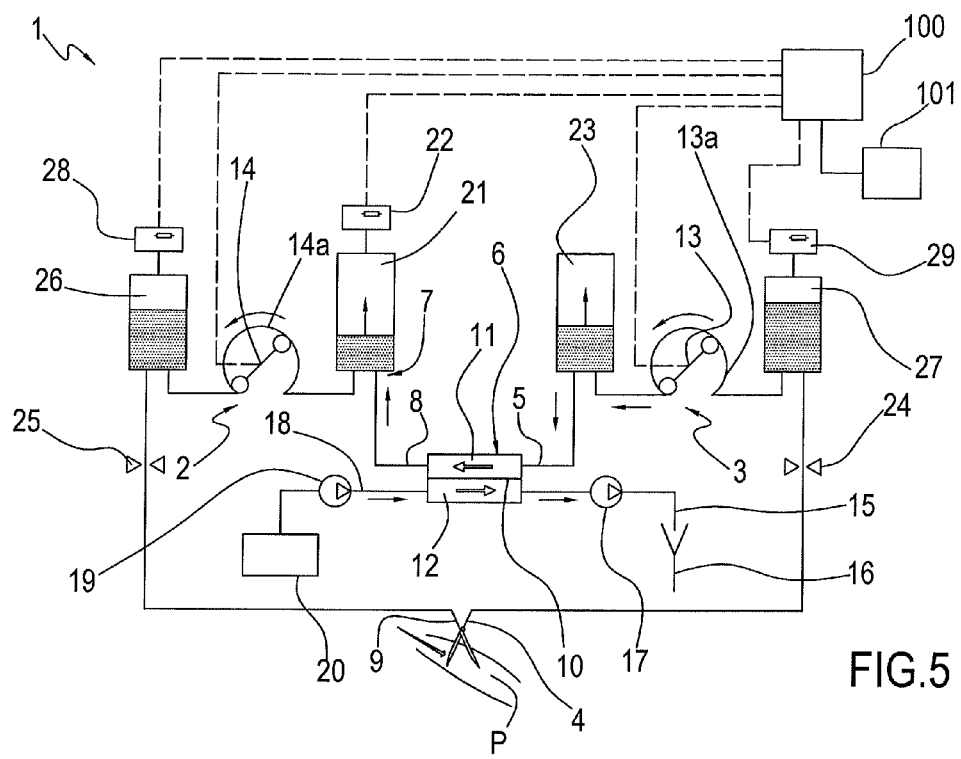
FIG. 5 is a schematic view of the extracorporeal blood treatment illustrated in FIG. 2 in a double-needle operating configuration.

In practice, in the first operating mode, the first and the second pumps are commanded and moved always in the same direction, but during sequential sub-stages:

a) in a first sub-stage the blood is removed from the patient—see FIG. 3: the first pump 13 rotates, while the second pump 14 is still, the first check organ 24 is open while the second organ 25 is closed; in this first sub-stage the first pump fills the first and the second reservoir;

b) in a successive and second sub-stage the blood is returned to the patient—see FIG. 4: the first pump 13 is still, while the second pump rotates, the first check organ 24 is closed, while the second check organ 25 is open.

In use conditions, the patient may be connected to the extracorporeal circuit in a single-access configuration. In some cases it might be necessary to pass from the single-access configuration to the double-access configuration. In these situations the operator may reconfigure the connection of the extracorporeal circuit and correspondingly inform the apparatus 1. For this purpose and in accordance with a further aspect, the control unit 100 may be predisposed to receive a command identifying the passage from a single vascular access configuration to a double vascular-access configuration: for example the command may be generated by a suitable input received from the user interface 101. Following this command, the control unit is configured to operate in the above-described second mode.

Lastly, the control unit is configured such as to receive, from the user interface, either a desired weight loss rate QWL or a pair of values relating to an overall weight loss WL and at a treatment time T in which to set the overall weight loss. The control unit controls the third pump or, if present, the ultrafiltration pump, according to the weight loss rate set or according to the pair of values relating to the overall weight loss and the treatment time such as to guarantee that the patient is subject to a certain weight loss during treatment.

Procedure

A further aspect of the invention relates to a blood treatment process, for example using an apparatus according to any one of the accompanying claims or according to what is described.

In the procedure the following steps are cyclically performed, when the extracorporeal circuit is configured for single-access:

commanding closure of the second check organ 25, commanding opening of the first check organ 24, moving the first pump 13 such as to command a fluid removal from the cardiovascular system of the patient through the removal line and the consequent increasing of the fluid level in the first and, if present, the second reservoir;

verifying the reaching of a predetermined maximum value of the parameter;

on reaching the predetermined maximum value of the parameter, commanding closure of the first flow check organ 24, halting of the first pump 13, opening of the second flow check organ 25 and movement of the second pump 14 with the aim of transferring fluid through the return line towards the cardiovascular system of the patient, and verifying the reaching of a predetermined minimum value of the parameter.

The process further comprises cyclically carrying out the following stages when it is required to pass from the single-access to the double-access configuration:

opening both the flow check organs 24 and 25 and controlling the first pump such as to promote movement of liquid from the first end 4 of the removal line towards the first chamber 11, controlling the movement of the second pump 14 in order to promote the blood return to the patient along the return line from the first chamber 11 towards the second end 9 of the return line 7; the control of the second pump is performed in such a way as to maintain the parameter detected by the sensor substantially constant or within a predetermined range of the parameter detected by the sensor 22. In a case where the parameter is the pressure, the angular velocity of the second pump is regulated by periodically verifying that the real pressure measured by the sensor 22 is substantially constant or lies within an acceptable pressure range.

Single-Use Disposable Set

Figure 7:
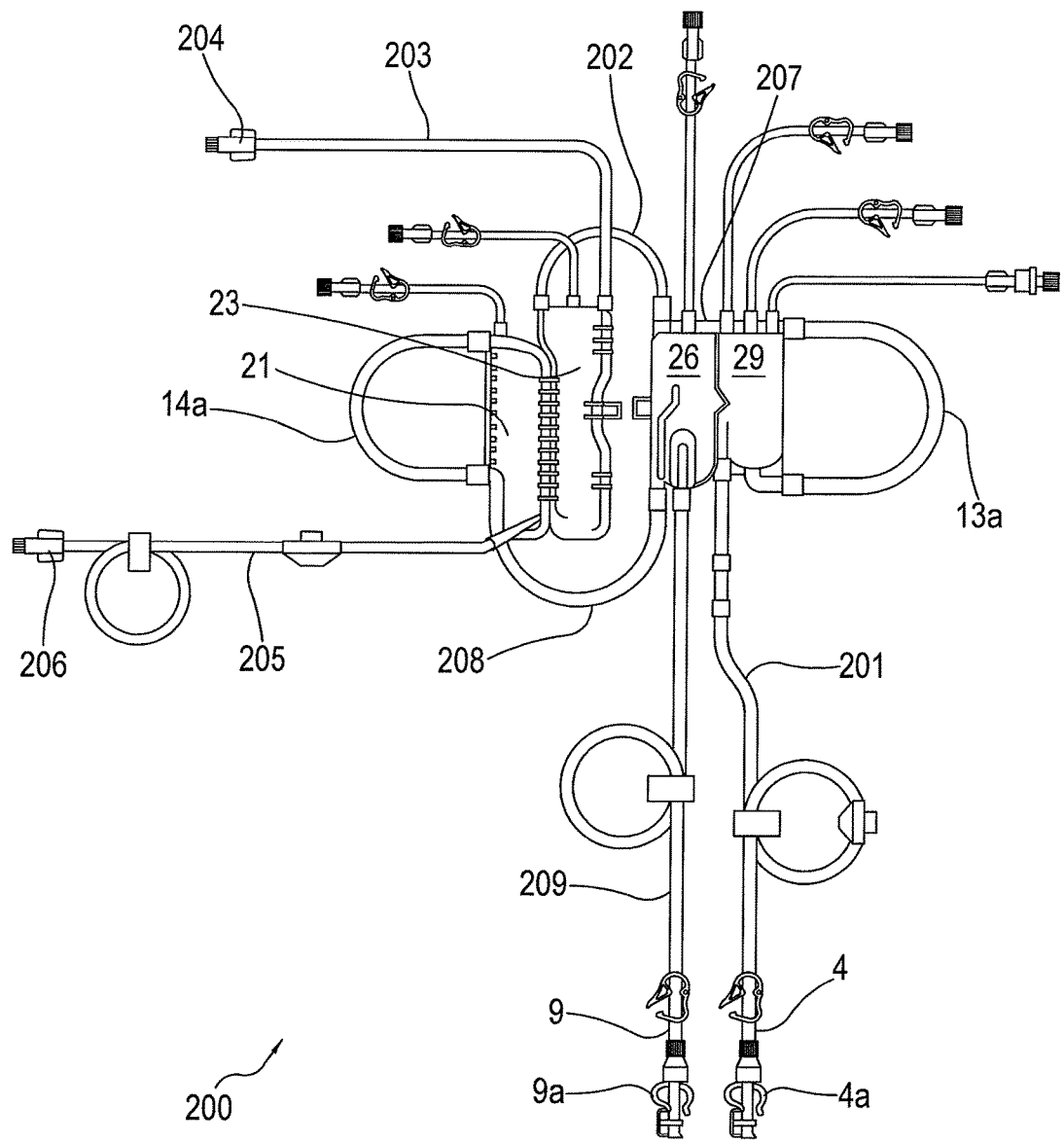
FIG. 7 is a single-use disposable set for forming an extracorporeal circuit of the apparatus of FIG. 2.

Note that the extracorporeal circuit 2 is in general defined by a single-use disposable set the use of which is limited in time. These sets comprise treatment units, tubes and reservoirs and various other accessories. FIG. 7 shows a set 200, for example of the single-use type, made of plastic material, for example transparent plastic material, which defines the whole extracorporeal blood circuit apart from the vascular accesses and the treatment unit. The set 200 of FIG. 7 comprises a first tube 201 which defines the tract of removal line 3 from the first end 4 up to the second auxiliary reservoir 27. The first tube 201 is connected to a connector located inferiorly of the second auxiliary reservoir which then joins a channel 207 located superiorly to the second auxiliary channel. This channel flows into the second tube 202 connected to an inlet borne by the second reservoir 23 which further exhibits an outlet which is connected with a third tube 203 terminally bearing a connector 204 for removable connection with an inlet port to the first chamber 11 of the treatment unit.

The set 200 further comprises a fourth tube 205 having a further terminal connector 206 for removable connection with an outlet port of the first chamber 11. The fourth tube 205 is connected in inlet to the first reservoir 21 which also exhibits an outlet connected to the pump tract 14a in turn connected to a fifth tube 208 which heads at an inlet connector of the first auxiliary reservoir 26. The auxiliary reservoir exhibits an outlet connector to which is connected a sixth tube 209 which terminates at the end 9 of the return line 7. At the ends 4 and 9 connectors 4a, 9a may be exhibited which are destined to removably couple with corresponding counter-connectors born by the vascular-access organ or organs. In the illustrated example the first and the second reservoirs are rigid and are defined by a single substantially flat body. Similarly the first and the second auxiliary reservoir are realised in a single plate-shaped body made of a rigid material.

Note that in the case of FIG. 1, the set which is usable may be without auxiliary reservoirs 26, 29.

While the invention has been described in connection with what is presently considered to be practical embodiments, it is to be understood that the invention is not to be limited to the disclosed embodiments, but on the contrary, is intended to cover various modifications and equivalent arrangements included within the spirit and the scope of the appended claims.

The invention claimed is:

1. An apparatus for extracorporeal blood treatment, comprising:
   a blood removal line having an end configured to be connected to a cardiovascular system of a subject;
   at least a blood treatment unit comprising a semipermeable membrane which divides the unit itself into a first and a second chamber, the first chamber being connected to a second end of the blood removal line;
   a blood return line, configured to return treated blood to the patient, the blood return line having a first end connected to the first chamber of the blood treatment unit and a second end configured to be connected to the cardiovascular system of the patient;
   at least a first pump operating on the blood removal line;
   at least a second pump operating at the blood return line to the patient;
   a discharge line connected to the second chamber of the treatment unit for receiving waste from the unit;
   at least a first blood reservoir operating on the blood return line upstream of the second blood pump;
   at least a sensor configured to detect at least a parameter selected from among a group consisting of:
      a pressure in the first reservoir,
      a blood level present in the first reservoir,
      a blood volume present in the first reservoir, and
      a pressure in a tract of the return line upstream the second blood pump,
   and configured to emit a signal corresponding to a measured value of the parameter;
      a control unit connected to the first pump, to the second pump and to the sensor, wherein the control unit is configured to operate in a first operating mode, corresponding to a single-access configuration of the extracorporeal circuit, and in a second operating mode, corresponding to a double-access configuration of the extracorporeal circuit, the control unit, in the second operating mode, being configured to carry out following steps:
      receiving the signal emitted by the sensor,
      controlling the first pump to promote the removal of blood from the patient along the blood removal line;
      controlling the second pump to promote return of the blood to the patient along the return line, the control of the second pump being carried out on the basis of the signal emitted by the sensor.

2. The apparatus of claim 1, comprising a second reservoir operating on the blood removal line from the patient and arranged upstream with respect to the first chamber and downstream of the first pump.

3. The apparatus of claim 2, further comprising a first flow check valve operating on the removal line upstream of the first pump and at least a second flow check valve operating on the blood return line to the patient downstream of the second pump, the control unit being connected to the first and second flow check valves and configured to selectively command opening and closure thereof and consequently to determine passage or the interdiction of the passage of fluid in the respective lines on which each of the first and second flow check valves operate.

4. The apparatus of claim 3, wherein the control unit in the first operating mode is configured to perform the following:
   a) commanding closure of the second flow check valve, commanding opening of the first flow check valve, moving the first pump to command a fluid removal from the cardiovascular system of the patient through the removal line and the consequent increasing of the fluid level in the first and the second reservoir, and verifying the reaching of a predetermined maximum value of the parameter;
   b) on reaching the predetermined maximum value of the parameter, commanding closure of the first flow check valve, halting of the first pump, opening of the second flow check valve and movement of the second pump with the aim of transferring fluid through the return line towards the cardiovascular system of the patient, and verifying the reaching of a predetermined minimum value of the parameter,
   c) on reaching the predetermined minimum value of the parameter, repeating a), b) and c).

5. The apparatus of claim 1, comprising at least a user interface connected to the control unit to communicate thereto input commands entered by an operator, the control unit, at least during the second operating mode, being configured to control the first pump according to a value selected from a group comprising:
   a. an input value set by an operator via the user interface,
   b. a measured pressure value prevailing in a tract of the blood removal line located upstream of the first pump,
   c. both said pressure value and the input value for blood flow entered by an operator via the user interface.

6. The apparatus of claim 1, wherein the control unit is configured to receive an identifying command of passage from a configuration with a single vascular access to a configuration with a double vascular access and wherein, following the command, further wherein the control unit is configured to operate in the second mode.

7. The apparatus of claim 1, wherein in the second mode, the control unit is configured to control the second pump in order to maintain the value of the parameter substantially constant or within a predetermined range.

8. The apparatus of claim 1, wherein the parameter is the pressure detected in the first reservoir.

9. The apparatus of claim 1, wherein the apparatus comprises at least a third pump acting on the waste line, the control unit being configured to receive, from the user interface, one from:
  a. a desired weight loss rate,
  b. a pair of values relating to an overall weight loss and to a treatment time in which the overall weight loss is to be attained,
    wherein the control unit is also configured to control the third pump either according to the weight loss rate or according to the pair of values relating to the overall weight loss and the treatment time.

10. The apparatus of claim 1, wherein the apparatus comprises at least a first auxiliary reservoir operating in the blood return line downstream of the tract thereof on which the second pump operates and at least a second auxiliary reservoir operating in the blood removal line in a tract thereof upstream of the tract where the first pump operates.

11. The apparatus of claim 10, wherein the apparatus comprises at least an auxiliary pressure sensor operated at the first auxiliary reservoir and at least a second auxiliary pressure sensor, operating at the second auxiliary reservoir, the first and second auxiliary sensors being connected to the control unit.

12. The apparatus of claim 1, wherein the control unit, in the second operating mode, is configured to carry out the following:
  a. commanding the first and the second flow check valves in open conditions;
  b. commanding the rotary movement of the first pump according to a set value of blood flow rate and/or a measured value of pressure in a tract of the removal line upstream of the tract in which the first pump operates;
  c. commanding the second blood pump in a rotary movement in the same direction as the rotary movement of the first blood pump, controlling the second pump to maintain the value of the parameter substantially constant or within a predetermined range.

13. The apparatus of claim 1, wherein the control unit, in the second operating mode, is configured to carry out the following:
  a. comparing a measured value of the parameter with a desired reference value for determining an error,
  b. generating a control value of the rotation velocity to be set on the second pump, the control value being generated as a function of the error,
  c. controlling the second pump, using the control value,
  d. repeating a, b, c.

14. The apparatus of claim 13, wherein the control value is determined as an integral function and/or as a proportional function of the error.

15. The apparatus of claim 14 wherein the control value is compared to a range of acceptability before being applied to the second blood pump.

16. A process of use of the apparatus of claim 1, the process comprising:
  configuring the extracorporeal circuit comprising the removal line and the return line in a single-access configuration,
  performing the removal and return of blood with respect to the cardiovascular system of the patient according to blood removal and return stages that are sequentially alternated,
  configuring the extracorporeal circuit in a double-access configuration,
  carrying out the blood removal and return by contemporaneously moving the first and the second pump in a same rotation direction to determine a continuous removal and return of the blood to the patient, and controlling the second pump to maintain the value of the parameter detected by the sensor substantially constant or within a predetermined range.

17. A process according to claim 16, comprising, when the extracorporeal circuit is in the single-access configuration:
  closing the second flow check valve;
  opening the first flow check valve;
  moving the first pump to command a fluid removal from the cardiovascular system of the patient through the removal line and the consequent raising of the fluid level in the first reservoir;
  verifying reaching of a predetermined maximum value of the parameter;
  on reaching the predetermined maximum value of the parameter, closing the first flow check valve, halting the first pump, opening the second flow check valve and moving of the second pump to transfer fluid through the return line towards the cardiovascular system of the patient, and verifying the reaching of a predetermined minimum value of the parameter.

18. A process according to claim 17 wherein changing from the single-access configuration to the double-access configuration comprises:
  opening both the flow check valve and controlling the first pump to promote movement of liquid from the first end of the removal line towards the treatment unit;
  moving the second pump to promote blood return to the patient along the return line from the treatment unit towards the second end of the return line;
  wherein the second pump is moved in such a way as to maintain the parameter detected by the sensor substantially constant or within a predetermined range.

19. A process according to claim 16, wherein the parameter is the pressure in the tract of the return line upstream the second blood pump, and wherein the angular velocity of the second pump is regulated by periodically verifying that the real pressure measured by the sensor is substantially constant or lies within an acceptable pressure range.

20. A process according to claim 1, wherein said sensor acts on the first reservoir.

21. A process according to claim 1, wherein the parameter is the pressure in the first reservoir and wherein said sensor acts on a line connected to said first reservoir.

* * * * *